(12) United States Patent
Roozen et al.

(10) Patent No.: US 9,695,102 B2
(45) Date of Patent: Jul. 4, 2017

(54) ALKALI METAL CINNAMATE POWDER AND METHOD FOR PREPARATION

(75) Inventors: Lambertus Hendricus Elisabeth Roozen, Gilze (NL); Elize Willem Bontenbal, Wageningen (NL); Nikolaos Vogiatzis, Gorinchem (NL); Brenda Marja Dierdorp-Andreas, Empel (NL)

(73) Assignee: Purac Biochem BV, Gorinchem (NL)

( * ) Notice: Subject to any disclaimer, the term of this patent is extended or adjusted under 35 U.S.C. 154(b) by 559 days.

(21) Appl. No.: 13/513,083

(22) PCT Filed: Dec. 2, 2010

(86) PCT No.: PCT/EP2010/068726
§ 371 (c)(1),
(2), (4) Date: Jul. 25, 2012

(87) PCT Pub. No.: WO2011/067330
PCT Pub. Date: Jun. 9, 2011

(65) Prior Publication Data
US 2012/0282468 A1    Nov. 8, 2012

(30) Foreign Application Priority Data
Dec. 3, 2009 (EP) .................... 09177870

(51) Int. Cl.
*C07C 69/76* (2006.01)
*B32B 5/16* (2006.01)
(Continued)

(52) U.S. Cl.
CPC .............. *C07C 57/44* (2013.01); *C07C 51/47* (2013.01); *C07C 69/612* (2013.01); *C07C 69/618* (2013.01); *Y10T 428/2982* (2015.01)

(58) Field of Classification Search
CPC ..... B01D 1/14; B01D 1/16; B01D 1/18; B01J 8/22; B01J 31/04; C07C 51/295;
(Continued)

(56) References Cited

U.S. PATENT DOCUMENTS 2,802,869 A * 8/1957 Montgomery ................ 562/495
3,345,263 A * 10/1967 Subbaratnam .......... C07C 57/60
424/497

(Continued)

FOREIGN PATENT DOCUMENTS

WO    WO 00/35850    6/2000
WO    WO 01/00312    1/2001

OTHER PUBLICATIONS

Wuhan Yuancheng Gongchuang Technology Co., Ltd., Potassium Cinnamate Chemical Raw Material (Sale brochure as of 2012).*

(Continued)

*Primary Examiner* — Holly Le
(74) *Attorney, Agent, or Firm* — Peter J. Ims; Westman, Champlin & Koehler, P.A.

(57) ABSTRACT

A method for the preparation of an alkali metal cinnamate powdery product, preferably potassium cinnamate or sodium cinnamate, is disclosed herein. The resulting product has novel structural properties. The powder of the present disclosure is made via spray-drying and/or spray agglomeration and has a higher flowability, is less cohesive and less dusty, has an improved dissolution rate and in particular has a very favorable organoleptic profile. The disclosure is also directed to product applications in which the novel cinnamate product of the present disclosure may be applied.

22 Claims, 1 Drawing Sheet

SEM picture - obtained via scanning electron microscope technique - of potassium cinnamate powder obtained via the method according to the present invention.

(51) Int. Cl.
*C07C 57/44* (2006.01)
*C07C 69/618* (2006.01)
*C07C 69/612* (2006.01)
*C07C 51/47* (2006.01)

(58) Field of Classification Search
CPC .......... C07C 51/43; C07C 69/612; C08J 3/03;
A61K 8/30; A61K 8/36; A61K 8/37;
A61K 8/58
USPC .............................. 34/329, 337, 343; 560/105
See application file for complete search history.

(56) References Cited

U.S. PATENT DOCUMENTS

| | | | |
|---|---|---|---|
| 4,609,756 A * | 9/1986 | Dorlars et al. | 562/495 |
| 4,687,761 A | 8/1987 | Liu | |
| 5,632,100 A * | 5/1997 | Hansen | 34/374 |
| 5,924,216 A * | 7/1999 | Takahashi | 34/374 |
| 6,051,256 A * | 4/2000 | Platz et al. | 424/489 |
| 6,294,186 B1 * | 9/2001 | Beerse et al. | 424/405 |
| 6,313,340 B1 | 11/2001 | Heidt | |
| 6,838,072 B1 | 1/2005 | Kong | |
| 2002/0007010 A1 | 1/2002 | Heidt | |
| 2006/0009435 A1 * | 1/2006 | Kaspi et al. | 514/179 |
| 2008/0154054 A1 * | 6/2008 | Klein et al. | 556/183 |
| 2009/0074927 A1 | 3/2009 | Bonorden et al. | |
| 2010/0137198 A1 * | 6/2010 | Eini et al. | 514/9 |

OTHER PUBLICATIONS

Elan Chemical Company, Inc., Material Safety Data Sheet, Potassium Cinnamate (printed Oct. 2007).*

European Search Report and Written Opinion of the European Patent Office Patent Office in counterpart foreign application No. PCT/EP2010/068726 filed Dec. 2, 2010.

Office Action issued in corresponding European Patent Application No. 09177870, dated Feb. 3, 2015 (four pages).

* cited by examiner

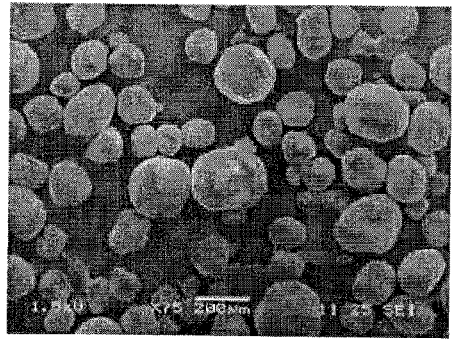
Figure 1: SEM picture – obtained via scanning electron microscope technique – of potassium cinnamate powder obtained via the method according to the present invention.
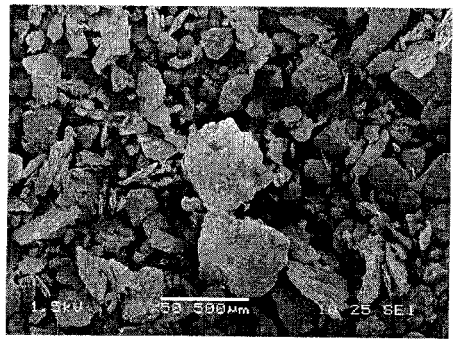
Figure 2: SEM picture of commercially available potassium cinnamate powder.

ALKALI METAL CINNAMATE POWDER AND METHOD FOR PREPARATION

CROSS-REFERENCE TO RELATED APPLICATION

This Application is a Section 371 National Stage Application of International Application No. PCT/EP2010/068726, filed Dec. 2, 2010 and published as WO 2011/067330 on Jun. 9, 2011, in English.

BACKGROUND

The discussion below is merely provided for general background information and is not intended to be used as an aid in determining the scope of the claimed subject matter.

An aspect of the present invention relates to a method for the preparation of an alkali metal cinnamate powdery product and to the product itself. Further, an aspect of the present invention is directed to product applications in which said alkali metal cinnamate product may be applied.

Alkali metal cinnamates such as for example potassium cinnamate and sodium cinnamate are known to be prepared via crystallization. A crystallization process is a costly and complex process. Crystallization processes require several liquid/solid-separation steps for separation of the crystals. The crystals further are treated in several wash- and drying steps. Additional processing steps are needed for treating the mother liquid and the various purge streams that are a result hereof. In all these steps the risk of potential product losses and yield losses is very high making the crystallization process complex and costly.

The crystallization process itself is known to be very difficult to control. This leads to a crystalline product that does not always have very favorable properties for the applications in which it is to be used. There is need for alkali metal cinnamates powders having improved flowability and dissolution properties. Further, crystalline potassium cinnamate for example is relatively cohesive and dusty. These unfavorable properties lead to practical and safety problems in handling and transporting of the crystalline product and in particular when looking at the dust explosion characteristics of for example potassium cinnamate. Further, significant amounts of products are lost in these operations as much product stays behind. It further requires additional expensive and time-consuming processing steps for cleaning the equipment and transport/packaging systems used.

There is thus a need for alkali metal cinnamate powdery products having improved physical properties with regard to properties such as e.g. dissolution behavior, dustiness, flowability and an improved stability. A solution to this problem was now found by preparing alkali metal cinnamates in a manner as described herein.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention hereto provides a new method for the preparation of an alkali metal cinnamate powdery product comprising a spray-drying and/or spray-agglomeration process. The new method comprising spray-drying and/or spray-agglomeration has various advantages in comparison to above-mentioned production method of crystallization. The new production method is very efficient, has a high product yield, has minimal product losses and low production costs and does not generate waste byproducts in contrast to precipitation/crystallization processes. Further, in the new production method according to aspects of the present invention no auxiliary materials are needed such as catalysts or washing agents and no separation, washing, drying or other processing steps are needed that are commonly present in crystallization processes.

The new production method is not complex and easy to (automatically) control and, as a consequence, a product of constant quality is achieved.

Preferably, alkali metal cinnamates such as for example sodium and/or potassium cinnamate are made using the method according to aspects of the present invention.

Using the spray-drying and/or spray-agglomeration process according to the present disclosure an alkali metal cinnamate powdery product, such as for example potassium cinnamate, is obtained having improved properties due to its new structural characteristics. These improved properties make the product easy to handle and transport unlike the present commercially available potassium cinnamate powders. Product losses in handling, transporting and packaging the powders are minimized and no additional cleaning of equipment and transport systems is necessary.

Further, as the properties of the product according to the present disclosure can be controlled, the product can be steered to have the properties that are of interest for a certain specific application. This broadens the field of possible applications to those applications in which up to now it was not possible or not very advantageous to use potassium cinnamate or sodium cinnamate. Some important examples are applications in the food and beverage industry or in the cosmetic field, in which for example potassium cinnamate could not be used due to its unfavorable (strong) organoleptic profile having an undesired impact on taste and odor. Further, the dustiness or stickiness of the potassium cinnamate powder can be controlled or steered.

BRIEF DESCRIPTION OF THE DRAWINGS

FIG. 1 is a picture of potassium cinnamate powder obtained via the method disclosed herein using a scanning electron microscope technique.

FIG. 2 is a picture of commercially available potassium cinnamate powder using a scanning electron microscope technique.

DETAILED DESCRIPTION

The method according to the present disclosure will be explained in the next parts of the present application using potassium cinnamate as an example. The method according to the present disclosure can also very well be applied for the manufacture of other alkali metal cinnamate powders, such as for example sodium cinnamate. In the remainder of this application, the reader accordingly may read alkali metal cinnamate or sodium cinnamate instead of potassium cinnamate.

The method according to the present disclosure for the preparation of a potassium cinnamate powder comprises atomizing a solution or slurry comprising potassium cinnamate to droplets and contacting the droplets with a heated gas to form solid potassium cinnamate particles followed by separating the solid particles from the gas.

In a preferred embodiment the method has the configuration of a spray-agglomeration process wherein the droplets are also contacted with solid potassium cinnamate particles to form agglomerates of solid potassium cinnamate particles followed by the separation of said agglomerates of solid particles from the gas.

The potassium cinnamate solution or slurry can comprise between about 10 to 50 wt % of potassium cinnamate. When referring to solutions, a concentration range of about 20 to 40 or 45 wt % at a temperature between about 50 and 80 to 100 degrees Celsius is applicable.

The method of the present disclosure may be performed in batch mode or continuously and can take place in the various well-known commercially available equipment for spray-drying and/or spray-agglomeration processes such as for example a spray-drying tower, a fluid bed dryer with an inlet for spraying the feed stream into the fluid bed dryer, a combination of both a spray-drying tower with a fluid bed dryer, the latter optionally integrated or placed externally as second drying phase, etc.

In a preferred embodiment of the present disclosure, the process is carried out in a spray tower in which the feed stream comprising the potassium cinnamate solution or slurry is atomized, preferably by using pressure nozzles, the atomized droplets are optionally contacted with potassium cinnamate fines while being dried by using air with an inlet temperature of about 100 to 250° C., more preferably around 170-190° C. The final temperature in the bottom part of the tower is about 60 to 100° C. and more preferably about 90 to 95° C. Said fines may originate from a classification system comprising sieves and optionally a milling step through which the dried solid potassium cinnamate particles are taken. The fines are then recycled back to the spray tower and brought in contact with the atomized potassium cinnamate droplets to form agglomerates.

In a further preferred embodiment of the present disclosure the process is carried out in a fluid bed dryer in which the feed stream comprising the potassium cinnamate solution or slurry is sprayed or atomized, preferably by using pressure nozzles, into a fluid bed comprising potassium cinnamate particles to form agglomerates while air is used for mixing and drying the particles and agglomerates. The air has an inlet temperature of about 100 to 250° C., more preferably around 110-150° C., most preferably 120-140° C. The final temperature in the bottom part of the tower is about 30 to 80 or 100° C. and more preferably about 50 to 60 or 70° C. Said fines may originate from a classification system comprising sieves and optionally a milling step through which the dried solid potassium cinnamate particles are taken. The fines are recycled back to the spray tower and brought in contact with the atomized potassium cinnamate droplets to form agglomerates.

Another option for conducting the method of the present disclosure may be by using a combination of a spray tower and a fluid bed dryer, the latter optionally being integrated in the bottom part of the tower.

The drying in above-mentioned process and equipment configurations may be followed by a classification system comprising sieves and optionally mills if more fine-tuning of the particle size is required. The fines after milling may be recycled back to the spray section of the spray tower or to the fluid bed section.

The potassium cinnamate solution or slurry that is used as feed for the spray-drying and/or spray-agglomeration process may be obtained by various means such as for example by means of chemical reaction, crystallization and/or precipitation.

The potassium cinnamate feed solution or slurry may for example be obtained via reaction of cinnamaldehyde with potassium carbonate. Cinnamaldehyde has however a very strong organoleptic profile in terms of taste and odor. The conversion process thus needs to be very efficient in terms of yield and the final potassium cinnamate product requires extensive purification in order to minimize the content of cinnamaldehyde as byproduct.

More preferably the potassium cinnamate feed solution or slurry is obtained via reaction of cinnamic acid with potassium hydroxide as this leads to potassium cinnamate having a much more preferable organoleptic profile with respect to taste and odor. In preparing the potassium cinnamate solution or slurry the pH is set at 8 to 10 and more preferably at around 8.5 to 9.5 (10 wt % solution).

In a further preferred embodiment, the method of the present disclosure comprises a further processing step directed to the treatment of potassium cinnamate with activated carbon. Preferably, this carbon treatment step takes place prior to feeding potassium cinnamate to the spray-drying and/or spray-agglomeration process. It was found that the combination of a carbon treatment with the method according the present disclosure provides a potassium cinnamate powdery product with minimal sensorial impact in terms of taste and odor. Compared to commercially available potassium cinnamate made via crystallization and based on using cinnamaldehyde, the potassium cinnamate product of the present disclosure displays a very favorable organoleptic profile. Contents of impurities such as e.g. benzaldehyde and cinnamaldehyde have been significantly decreased to a factor 3 or more and even to a factor 7.

It is a further objective of the invention to provide a new potassium cinnamate product. The product not only displays an improved organoleptic profile but the product is novel in the sense that it has new structural characteristics which result in a (controllable) less dusty and less cohesive powdery product with high flowability and favorable dissolution rates compared to commercially available potassium cinnamate product.

The method as described herein yields a potassium cinnamate powder that is free-flowing and comprising nicely almost round shaped or spherical particles in contrast to commercially available potassium cinnamate. The latter commercial products comprise particles having many edges, looking more like cubical- and/or rod- and/or pyramid-shaped blocks or having a form in between. These rod- or pyramid- or cubical-shaped particles are an indication that said particles are made via crystallization processes. The nicely spherical-shaped spray-dried potassium cinnamate particles of the present disclosure have a much narrower particle size distribution as compared to commercially available products.

Particle sizes of the powder may be controlled and steered to a desired size and/or size distribution. The particle size may be between 100 and a 1000 micrometers. Preferably, the d50 may be between 250 and 450 micrometers. Depending on the application in which the potassium cinnamate is to be used, the particles may be given the appropriate required particle size and/or size distribution. The favorable characteristics of the novel less dusty powdery product of the present disclosure make the potassium cinnamate product very accessible in the sense that it may be handled more easily with less expensive equipment and less restrictive explosion safety requirements.

Thus, the present disclosure provides a potassium cinnamate powdery product comprising potassium cinnamate particles wherein the ratio of the largest diameter to the smallest diameter of the particles is at the most 1.3, preferably at the most 1.2, more preferably at the most 1.1. Preferably, at least 80%, more preferably at least 90%, of the potassium cinnamate particles fulfils this ratio requirement. The d50 of the particles preferably may be between 250 and 450 micrometers.

The potassium cinnamate powdery product of the present disclosure further has a Hausner ratio (a well-known parameter to express or indicate the degree of flowability) of at the most about 1.2, preferably at the most about 1.15. A potassium cinnamate powdery product having such a Hausner ratio is easier to transport and to handle and the caking tendency is less than with commercially available potassium cinnamate. A Hausner ratio of higher than 1.4 means, as known to the person skilled in the art of powders, that the powder is very cohesive and thus more difficult to handle or even not suited at all for proper handling and transport. Commercially available potassium cinnamate made via crystallization was measured to have a very poor flowability represented by a Hausner ratio of about 1.66 which is very poor. The very good flowability of the potassium cinnamate powder of the present disclosure is also demonstrated by an angle of repose of at the most about 36 degrees and an angle of spatula of at the most about 48 degrees. As the person skilled in the art of powders is well aware of, the smaller or steeper these angles are, the better the flowability of the powder is. In general, an angle of repose of below 40 degrees and an angle of spatula of below 50 degrees indicates a good flowability.

Due to the advantageous novel structural properties of the potassium cinnamate powdery product of the present disclosure, this product was found to be very suitable for various product applications such as cosmetic and personal care applications, and technical applications. Due to its favorable organoleptic profile, the potassium cinnamate powder according to the present disclosure may in particular be used for preservation purposes in various products in the field of food and drinks in which until now potassium cinnamate could not be used because of its negative sensorial impact on taste and flavor and/or odor.

Similar for application of the novel potassium cinnamate product in cosmetic applications such as for example lotions and creams in which before potassium cinnamate could not be used because of its negative impact on odor.

The following non-limiting examples illustrate aspects of the invention.

EXPERIMENTS

Experiment 1

Example of Preparation of Potassium Cinnamate Via a Spray-Drying Process

A solution comprising about 14.5 wt % potassium cinnamate is made via reaction in an aqueous environment of an aqueous 50 wt % potassium hydroxide solution with pure cinnamic acid powder at a final pH of about 8.5 to 9.5 for a 10 wt % solution. The solution was fed to a commercially available spray dryer. The solution was fed with an ingoing temperature of about 55° C. and atomized by means of using pressure nozzles (~30 bar). The spray of droplets was brought in contact with heated air with an inlet temperature of about 180° C. The outlet temperature was about 95° C.

The resulting potassium cinnamate powder had an average moisture content of about less than 2 wt %.

Experiment 2

Example of Preparation of Potassium Cinnamate via a Process with Spray-Agglomeration Configuration A solution comprising about 20 wt % potassium cinnamate is made via reaction in an aqueous environment of an aqueous 50 wt % potassium hydroxide solution with pure cinnamic acid powder at a final pH of about 8.5 to 9.5 for a 10 wt % solution. The solution was fed to a commercially available continuous fluid bed dryer. The solution was fed with an ingoing temperature of about 55° C. and atomized using a two-fluid nozzle at 1.5 bar. The spray of droplets was brought in contact with potassium cinnamate granules in a fluidized bed to form agglomerates. Heated air with an inlet temperature of about 130° C. was used for fluidization of the bed and simultaneous drying of the agglomerates. The bed temperature was about 36° C.

The resulting potassium cinnamate powder had an average moisture content of about 0.5 wt % and an average particle size of 200 to 500 micrometer.

Comparison Commercially Available Potassium Cinnamate Solutions with Carbon-Treated Potassium Cinnamate Spray-dried/agglomerated According to the Present Disclosure SEM Photo's SEM pictures of the potassium cinnamate powder obtained via the method according to the present disclosure showed almost completely round or spherical shaped particles (some agglomerated together) as shown in FIG. 1 in contrast to commercially available potassium cinnamate powder (FIG. 2).

Particle Size Distributions

Particle size distribution has been measured with a Malvern Mastersizer 2000® particle size analyzer Measurement. Measuring principle is based on laser diffraction. Results are shown in the following Table 1.

TABLE 1

| Sample name | Particle size distribution | | | | | |
| --- | --- | --- | --- | --- | --- | --- |
| | D (0.1) | D (0.5) | D (0.9) | D [3.2] | D [4.3] | Span (—) |
| Potassium cinnamate of the present disclosure | 114 | 192 | 320 | 178 | 206 | 1.07 |
| Potassium cinnamate commercially available | 44 | 240 | 601 | 89 | 286 | 2.32 |

The powder of the present disclosure shows a relatively narrow particle size distribution in contrast to commercially available potassium cinnamate powder.

Measurement of the the Hausner Ratio and Angle of Repose and the Angle of Spatula These are all standard measurements described in various text and hand books on powders and their properties. The various measurements were done using a Micron Powder Characteristics Tester™ (Model PT-N) from Hosokawa Micron International Inc.

The Hausner ratio is determined by measurement of the tapped and untapped (or aerated) bulk density. The angle of repose is determined by measurement of the angle of a cone of powder that is formed by pouring the powder through a glass funnel.

The angle of spatula is determined by measurement the difference in the angle of powder—that stays behind on a spatula when a container with said spatula on the bottom and filled with said powder is lowered and the spatula stays on the same height—and the angle of the powder on said spatula after the spatula was tapped by a weight.

The results are summarized in the following Table 2.

TABLE 2

Measured properties of potassium cinnamate powder obtained via present disclosure and of commercially available potassium cinnamate

| Sample | Aerated Bulk Density (kg m$^{-3}$) | Tapped Bulk Density (kg m$^{-3}$) | Hausner Ratio | Carr class | Angle of repose [index] | | Angle of spatula [index] | |
|---|---|---|---|---|---|---|---|---|
| Potassium cinnamate of the present disclosure | 823 | 945 | 1.15 | Good | 35.6 | good | 48 | normal |
| Potassium cinnamate commercially available | 318 | 527 | 1.66 | Very poor | | | | |

The "Carr class" is a known index or scale (R. I. Carr, 1965, Evaluation of flow properties of solids) based on compaction and used to compare the flow properties of various powders with each other. The expressions "good" and "fairly good" on this scale indicate that the potassium cinnamate powder of the present disclosure is very well free-flowing in contrast to the commercially available potassium cinnamate lactate powder. It further indicates that in handling and transporting the powder, e.g. packaged in big bags, the powder is not significantly compressed. As a consequence, the big bags are not suddenly "half empty" when they reach the customer.

The invention claimed is:

1. A method for the preparation of an alkali metal cinnamate powdery product comprising atomizing a solution or slurry comprising alkali metal cinnamate to droplets and contacting the droplets with heated gas to form solid alkali metal cinnamate particles followed by separating the solid particles from the gas, where in the solution or slurry of alkali metal cinnamate is obtained by the reaction of unsubstituted cinnamic acid with alkali metal hydroxide.

2. The method according to claim 1 wherein the gas is air.

3. The method according to claim 1 wherein said cinnamic acid is reacted with alkali metal hydroxide in an aqueous environment to obtain a solution or slurry of alkali metal cinnamate having a pH of from 8 to 10.

4. The method according to claim 1 wherein said alkali metal cinnamate is potassium cinnamate or sodium cinnamate, and wherein said solution or slurry comprising potassium cinnamate or sodium cinnamate is obtained by the reaction of said cinnamic acid with potassium hydroxide or sodium hydroxide.

5. The method according to claim 4 wherein the potassium cinnamate solution or slurry comprises 10-50 wt % of potassium cinnamate.

6. The method according to claim 1 wherein the droplets are also contacted with solid particles of the same alkali metal cinnamate as the droplets to form agglomerates of solid alkali metal cinnamate particles followed by the separation of said agglomerates of solid particles from the gas.

7. An alkali metal cinnamate powder obtained by the method according to claim 6, said powder comprising alkali metal cinnamate particles, the particles having a ratio of the largest diameter to the smallest diameter of at the most 1.3, the powder having a Hausner ratio of at the most 1.2.

8. The method according to claim 1 further comprising treating the solution or slurry with activated carbon prior to atomizing.

9. An alkali metal cinnamate powder obtained by the method according to claim 8, said powder comprising alkali metal cinnamate particles, the particles having a ratio of the largest diameter to the smallest diameter of at the most 1.3, the powder having a Hausner ratio of at the most 1.2.

10. An alkali metal cinnamate powder obtained by the method according to claim 1, said powder comprising alkali metal cinnamate particles, the particles having a ratio of the largest diameter to the smallest diameter of at the most 1.3, the powder having a Hausner ratio of at the most 1.2.

11. The alkali metal cinnamate powder of claim 10, wherein the particle size of the alkali metal cinnamate particles is between 100 and 1000 micrometers.

12. The alkali metal cinnamate powder of claim 10, wherein the $d_{50}$ of the alkali metal cinnamate particles is between 250 and 450 micrometers.

13. The alkali metal cinnamate powder of claim 10, wherein the alkali metal is potassium.

14. The alkali metal cinnamate powder of claim 10 and wherein the powder is used in personal care, cosmetic or technical product applications and/or food and/or beverage applications.

15. An alkali metal cinnamate powder of claim 10 and wherein the particles having a ratio of the largest diameter to the smallest diameter of at the most 1.2.

16. An alkali metal cinnamate powder of claim 10 and wherein the particles having a ratio of the largest diameter to the smallest diameter of at the most 1.1.

17. A method for the preparation of an alkali metal cinnamate powdery product having an improved organoleptic profile with respect to taste and color, the method comprising atomizing a solution or slurry comprising alkali metal cinnamate to droplets and contacting the droplets with heated gas to form solid alkali metal cinnamate particles followed by separating the solid particles from the gas, where in the solution or slurry of alkali metal cinnamate is obtained by the reaction of unsubstituted cinnamic acid with alkali metal hydroxide.

18. The method according to claim 17 wherein said alkali metal cinnamate is potassium cinnamate or sodium cinnamate, and wherein said solution or slurry comprising potassium cinnamate or sodium cinnamate is obtained by the reaction of said cinnamic acid with potassium hydroxide or sodium hydroxide.

19. The method according to claim 18 wherein the potassium cinnamate solution or slurry comprises 10-50 wt % of potassium cinnamate.

20. The method according to claim 17 wherein the droplets are also contacted with solid particles of the same alkali metal cinnamate as the droplets to form agglomerates of solid alkali metal cinnamate particles followed by the separation of said agglomerates of solid particles from the gas.

21. The method according to claim 17 further comprising treating the solution or slurry with activated carbon prior to atomizing.

22. The method according to claim 17 wherein said cinnamic acid is reacted with alkali metal hydroxide in an aqueous environment to obtain a solution or slurry of alkali metal cinnamate having a pH of from 8 to 10.

* * * * *